United States Patent [19]
Sugiura

[11] Patent Number: 5,551,423
[45] Date of Patent: Sep. 3, 1996

[54] PULSE OXIMETER PROBE

[75] Inventor: Keiichi Sugiura, Tokyo, Japan

[73] Assignee: Nihon Kohden Corporation, Tokyo, Japan

[21] Appl. No.: 487,225

[22] Filed: Jun. 7, 1995

Related U.S. Application Data

[63] Continuation of Ser. No. 186,526, Jan. 26, 1994, abandoned.

[30] Foreign Application Priority Data

Jan. 26, 1993 [JP] Japan ................................. 5-001607 U
Jan. 26, 1993 [JP] Japan ................................. 5-001609 U

[51] Int. Cl.⁶ ..................................................... A61B 5/00
[52] U.S. Cl. ............................. 128/633; 128/665; 356/41
[58] Field of Search ............................... 128/633, 664–6, 128/41; 356/41

[56] References Cited

U.S. PATENT DOCUMENTS

| | | | |
|---|---|---|---|
| 3,810,460 | 5/1974 | Van Nie | 128/666 |
| 4,334,544 | 6/1982 | Hill et al. | 128/666 |
| 5,112,124 | 5/1992 | Harjunmaa et al. | 128/633 |
| 5,247,931 | 9/1993 | Norwood | 128/633 |
| 5,279,295 | 1/1994 | Martens et al. | 128/633 |

FOREIGN PATENT DOCUMENTS 9216142 10/1992 WIPO ..................................... 128/633

*Primary Examiner*—Angela D. Sykes
*Assistant Examiner*—Robert L. Nasser, Jr.
*Attorney, Agent, or Firm*—Sughrue, Mion, Zinn, Macpeak & Seas

[57] ABSTRACT

A pulse oximeter probe includes a measuring member including a light-emitting element and a light receiving element, a pair of holding members for holding the basal part of an earlobe, the measuring member mounted on the holding member, the holding members including compressing portions for holding the basal part of the earlobe, the compressing portions being separated in position from the measuring member.

7 Claims, 5 Drawing Sheets

PULSE OXIMETER PROBE

This is a Continuation of application Ser. No. 08/186,526 filed Jan. 26, 1994, now abandoned.

BACKGROUND OF THE INVENTION

1. Field of the Invention

This invention relates to a pulse oximeter probe that detects the pulsation or throbbing of blood flowing through a blood vessel in the living body so as to measure the oxygen saturation of blood and other blood-related parameters. The invention relates particularly to a pulse oximeter probe of a type that is to be attached to the ear of a subject.

2. Related Art

Conventional pulse oximeter probes which are to be used for measuring the oxygen saturation of blood and other blood-related parameters in the living body are available in two types depending on the mechanism for detecting the pulsation of blood flowing through blood vessels, i.e., by light transmission through the probe that is attached to a subject's finger, leg or earlobe or by light reflection from the probe that is attached to the forehead of the subject having a comparatively large amount of blood circulation.

A problem with the type of probe that is to be attached to a subject's finger or leg is that the subject is no longer free to use both hands or finds difficulty in walking. Furthermore, it is difficult for the analyst to acquire consistent data. On the other hand, less inconvenience will be caused to the life of the subject if the probe is attached to his earlobe.

A conventional pulse oximeter probe of the type that is to be attached to the earlobe is typically in the form of a clip. As shown in FIGS. 13 and 14, the probe comprises generally a pair of holding members 21 and 22 that are connected together at an end in such a way that they can pivot on a shaft 23. The holding members 21 and 22 are furnished with a light-emitting device 24 and a light-receiving device 25, respectively, in such a way that they are in a face-to-face relationship. The shaft 23 is fitted with a leaf spring (not shown) that urges the devices 24 and 25 to pivot in a direction in which they approach each other. The probe generally indicated at 27 can be attached to the earlobe 26 of a subject by holding it with the holding members 21 and 22.

However, the conventional oximeter probe of the clip type which is constructed in the manner just described above has two major drawbacks. First, the holding members 21 and 22 have to compress the earlobe 26 so as to detect the pulsation of blood flowing in the compressed area but, then, the quantity of blood circulation decreases to lower the precision of measurement. Second, the probe 27 which is attached to the earlobe 26 is liable to movements and, hence, errors due to the movement of the earlobe are most likely to occur if measurements are done while the subject is walking.

SUMMARY OF THE INVENTION

The present invention has been accomplished under the circumstances and has as an object providing a pulse oximeter probe that can be attached to the ear of a subject without compressing the site of measurement, that is less sensitive to unwanted movements of a body part such as the neck and which hence is capable of precise measurements.

This object of the present invention can be attained by the pulse oximeter probe that is recited in claim 1 and which detects the pulsation of blood in a blood vessel by reception of light at a light-receiving element after it is transmitted through a part of the living body following its emission from a light-emitting element. There is provided that a probe comprises a pair of holding members for holding the basal part of the earlobe of a subject and a measuring section that consists of the light-emitting and light-receiving elements which are provided on the respective holding members in a face-to-face relationship and further provided that the compressing portions which hold the basal part of the earlobe are each separated in position from the measuring section.

This probe may be modified as recited in claim 2, wherein one of the two holding members forms at an end a bent portion that can be inserted into the entrance to the auditory meatus and wherein the measuring section is composed by providing the light-emitting element in either the compressing portion or the bent portion of the other holding member while the light-receiving element is provided in either the bent portion or the compressing portion in such a way that it is in a face-to-face relationship with the light-emitting element.

The probe may further be modified as recited in claim 3, wherein one of the two holding members is fitted with a connecting shaft at the connecting end and wherein the connecting shaft is inserted slidably into a slot that is formed at the connecting end of the other holding member.

The above-stated object of the present invention can be attained by a pulse oximeter probe that detects the pulsation of blood in a blood vessel by reception of light at a light-receiving element after it is transmitted through a part of the living body following its emission from a light-emitting element, which probe is provided by comprising a holding member that is formed of an elastic material in a generally semicircular form, a measuring section that consists of the light-emitting and light-receiving elements which are provided at opposite ends of the holding member in a face-to-face relationship, and an engaging member the basal end of which is fitted rotatably at an end of the holding member and which has in the middle part a projection that presses the upper part of a subject's ear for holding it in position, with another projection being formed at the distal end in such a way that it is capable of engagement with the other end of the holding member.

The probe according to the present invention, the distal end of the bent portion formed on one of the two holding members is inserted near the entrance to the auditory meatus and the basal part of the earlobe is held by means of the compressing portions which are provided on the pair of holding members, whereby the probe can be securely attached to the ear. This insures that even if the subject makes movement as in walking, the probe will not move an unduly great amount, thereby enabling the intended measurement to be accomplished with high precision. What is more, the portion of the probe that compresses the ear in order to achieve secure attachment and the portion that transmits light for measurement differ in position and, hence, blood vessels at the site of measurement will in no way be compressed and this contributes to a further enhancement in the precision of measurement.

Further, the pair of holding members are connected together by means of the shaft which is inserted into the slot and, hence, when the ear is held by the two holding members with the distal end of the bent portion of one holding member being inserted into the auditory meatus, the compressing portions can hold the basal part of the earlobe in positions that comply with the surface profile of that basal part. As a result, the probe can be attached to the earlobe in an easy but positive manner.

To use the probe of the present invention, the holding member is placed on the upper part of a subject's ear in such a way that the light-emitting and the light-receiving elements are positioned in a face-to-face relationship, with the ear being interposed; thereafter, the engaging member is turned pivotally until the projection at the distal end is brought into engagement with the holding member, whereby the probe can be attached to the ear in a stable manner. Further, the light-emitting and the light-receiving element are kept apart by the engaging member, with the ear being interposed, and blood vessels in the ear will not be compressed, thus insuring measurements to be accomplished with high precision.

DETAILED DESCRIPTION OF THE PREFERRED EMBODIMENTS

The pulse oximeter probe according to a first embodiment of the present invention is described below with reference to accompanying drawings.

First Embodiment

Figure 1:
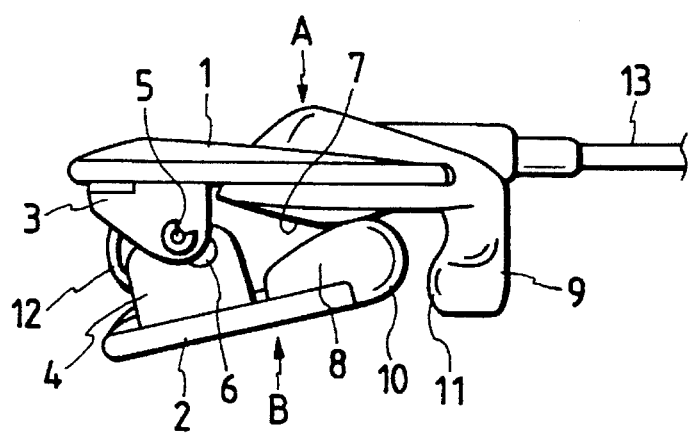
FIG. 1 is a side view showing the construction of a pulse oximeter probe according to a first embodiment of the present invention.
Figure 2:
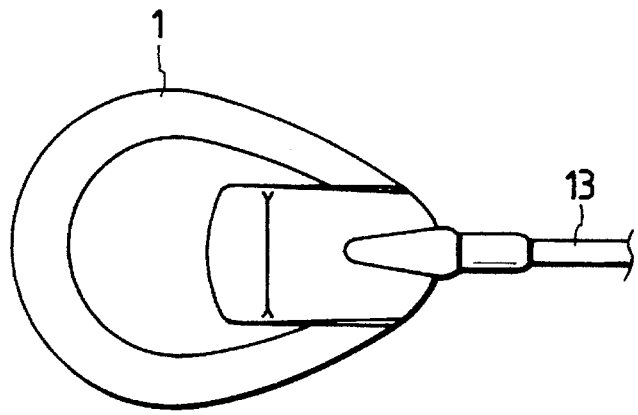
FIG. 2 is a view of the probe as seen in the direction indicated by arrow A.
Figure 3:
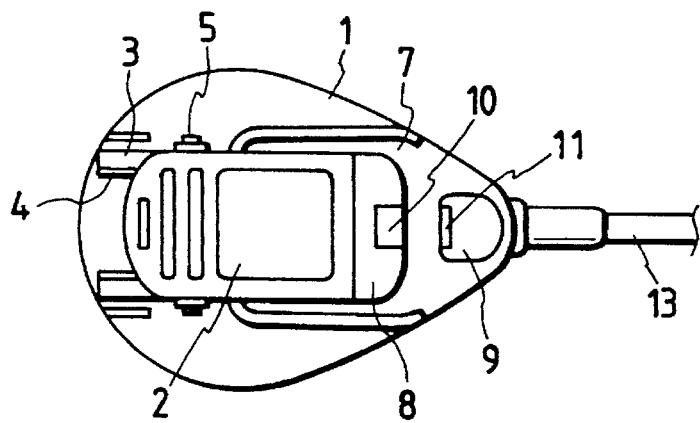
FIG. 3 is a view of the probe as seen in the direction indicated by arrow B.

FIGS. 1 to 3 show the construction of the probe according to the first embodiment of the invention. It has a pair of holding members 1 and 2 which are provided with ribs 3 and 4, respectively, at an end, and the ribs 3 on one holding member 1 are fitted with a shaft 5. A slot 6 is formed in the ribs 4 on the other holding member 2 and a shaft 5 is inserted through the slot 6. A compressing portion 7 is formed in the middle part of the holding member 1 and another compressing portion 8 is formed at the distal end of the holding member 2 in such a way that they form projections in a face-to-face relationship. The shaft 5 is fitted with a leaf spring (not shown) to urge the compressing portions 7 and 8 in a direction that causes them to contact each other.

The holding member 1 has a bent portion 9 formed at an end opposite the side where the ribs 3 are formed and this bent portion 9 is directed towards the holding member 2. The opposing faces of the compressing portion 8 and the bent portion 9 are provided with a light-emitting element 10 and a light-receiving element 11, respectively, that combine to compose the measuring section. The light-emitting element 10 and the light-receiving element 11 are connected to an external measuring instrument (not shown) via respective leads 12 and 13.

Figure 4:
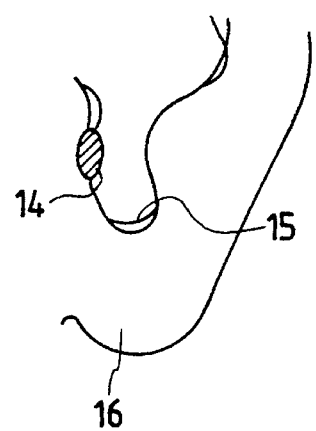
FIG. 4 is a sketch of an ear showing the position in which the bent portion of the probe is to be attached to the ear.
Figure 5:
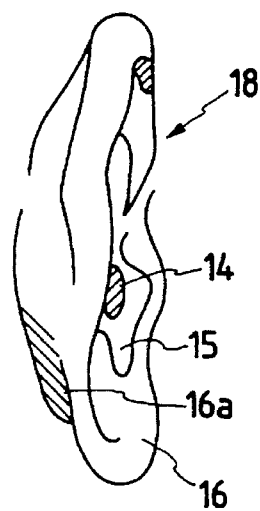
FIG. 5 is a sketch of an ear showing the position in which the compressing portions of the probe are to be attached to the ear.
Figure 6:
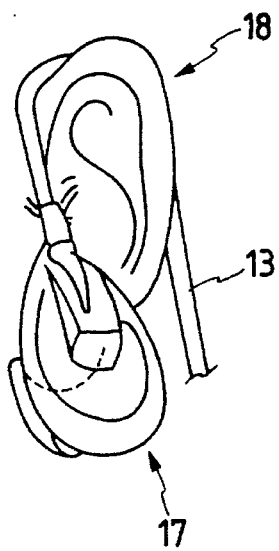
FIG. 6 is a sketch of the probe as it is attached to the ear.

The use and operation of the probe under consideration is described below with reference to FIGS. 4 to 6. First, the distal end of the bent portion 9 shown in FIG. 1 is inserted for engagement with a U-shaped area 15 at the entrance to the auditory meatus of a subject's ear which is shown in FIG. 4. Then, the compressing portions 7 and 8 are brought into contact with opposite sides of the basal part 16a of the earlobe 16 which is shown in FIG. 5, whereby it is held by means of the holding members 1 and 2. Since the shaft 5 is movable along the slot 6 in the sliding member 2, the user may adjust the positions of compressing members 7 and 8 slightly in conformity with the surface profile of his ear 18 so that the probe 17 can be attached securely by means of the holding members 1 and 2. The probe will not compress blood vessels at the site of measurement since the light-emitting element 10 and the light-receiving element 11 merely contact the basal part 16a of the subject's earlobe 16 and the inside of the U-shaped area 15 at the entrance to the auditory meatus. The light issuing from the element 10 passes through the ear 18 to be received by the element 11 for detecting the pulsation of blood flowing in blood vessels in the ear 18. Based on the pulsation of blood, the analyst can determine its oxygen saturation, pulse wave, pulse rate, blood pressure and other blood-related parameters. To secure the attachment of the probe, the lead 13 may be bent around the back of the ear 18.

When the probe 17 is attached to the ear 18, the compressing portions 7 and 8 compress and hold the basal part 16a of the earlobe 18 in different positions than the measuring section which consists of the light-emitting and light-receiving elements 10 and 11 which are disposed in a face-to-face relationship and, hence, the pulsation of blood flowing in blood vessels at an uncompressed site of measurement can be detected with high precision. Further, the probe 17 is attached to the ear while holding the basal part 16a of the earlobe 16 in position and this insures the intended measurement to be done in a consistent manner since the probe 17 will not move greatly even if the subject makes movement as in walking. Another advantage of attaching the probe 17 to the subject's ear 18 is that he or she is free to use both hands.

The first example described above concerns the case where the light-emitting element 10 is provided in the compressing portion 8 whereas the light-receiving element 11 is provided in the bent portion 9; if desired, the arrangement may be reversed and the light-emitting element 10 is provided in the bent portion 9 whereas the light-receiving element 11 is provided in the compressing portion 11.

As described on the foregoing pages, the pulse oximeter probe according to the first embodiment of the present invention is capable of precise detection of blood pulsation without compressing blood vessels at the site of measurement since the compressing portions by means of which the probe is attached to the subject's ear differ in position than the measuring section which is composed of the light-emitting and light-receiving elements in a face-to-face relationship. Another advantage that results from the attachment of the probe to the basal part of the subject's earlobe is that consistent measurements can be accomplished even if the subject makes movement as in walking.

Second Embodiment

The pulse oximeter probe according to a second embodiment of the present invention is described below with reference to accompanying drawings.

Figure 7:
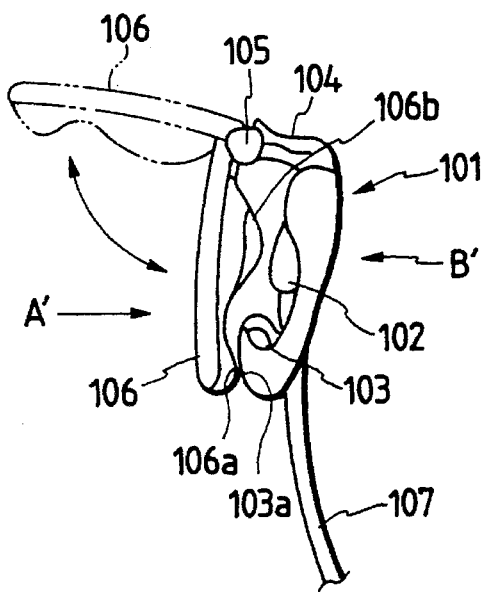
FIG. 7 is a side view showing the construction of a pulse oximeter probe according to a second embodiment of the present invention.
Figure 8:
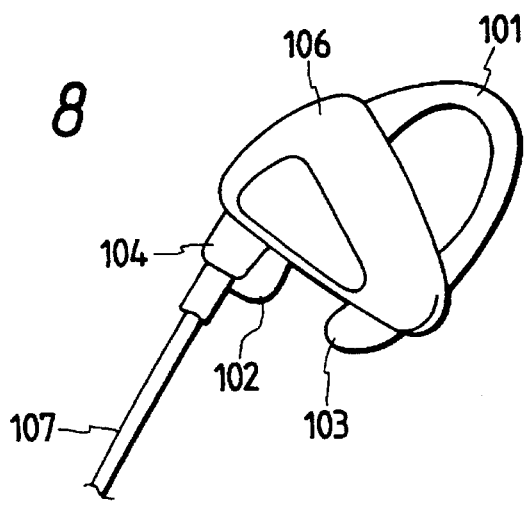
FIG. 8 is a view of the probe as seen in the direction indicated by arrow A.
Figure 9:
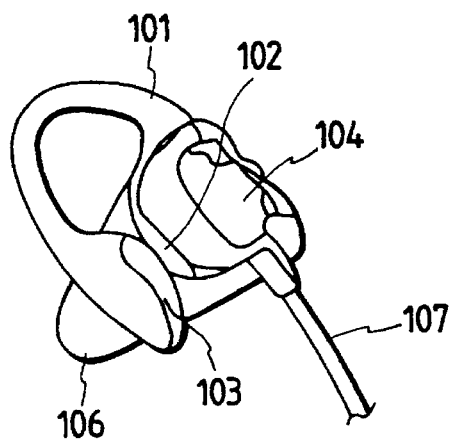
FIG. 9 is a view of the probe as seen in the direction indicated by arrow B.

FIGS. 7 to 9 show the construction of the probe according to the second embodiment of the invention. It has a holding member 101 that is formed of an elastic material in a generally semicircular form; the holding member 101 has a light-emitting element 102 and a light-receiving element 103 at opposite ends as disposed in a face-to-face relationship. A metal fixture 104 is secured to the end portion of the holding member 101 where the light-emitting element 102 is provided. A generally triangular engaging member 106 is mounted on the metal fixture 104 in such a way that the base of the member 106 can pivot on a shaft 105.

The engaging member 106 has at its distal end a first pad portion 106a which is engageable with a recess 103a formed in the lateral side of the light-receiving element 103; the engaging member 106 also has a second pad portion 106b which presses the subject's ear against the lateral side of the light-emitting element 102. The engaging member 106 is urged by a leaf spring (not shown) in such a way that it pivots in a direction that causes the second pad portion 106b to approach the lateral side of the light-emitting element 102. The light-emitting and light-receiving elements 102 and 103 are connected to an external measuring instrument via a lead 107.

Figure 10:
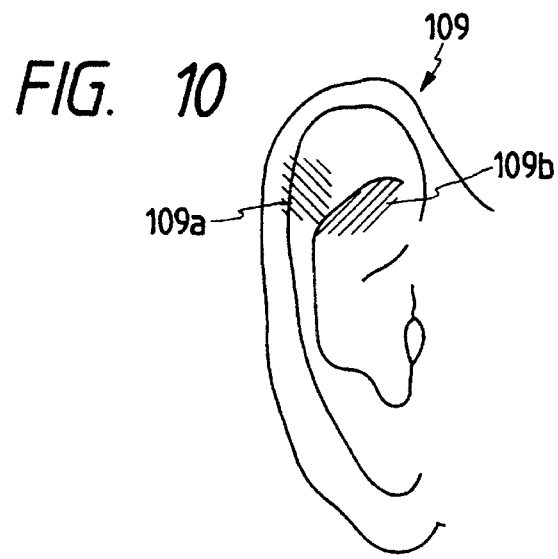
FIG. 10 is a sketch of the front side of a subject's ear showing the position in which the probe is to be attached to the ear.
Figure 11:
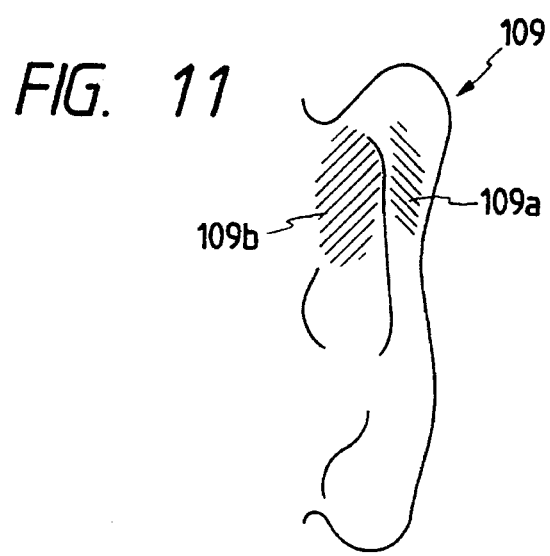
FIG. 11 is a sketch of the back side of the ear showing the position in which the probe is to be attached to the ear.
Figure 12:
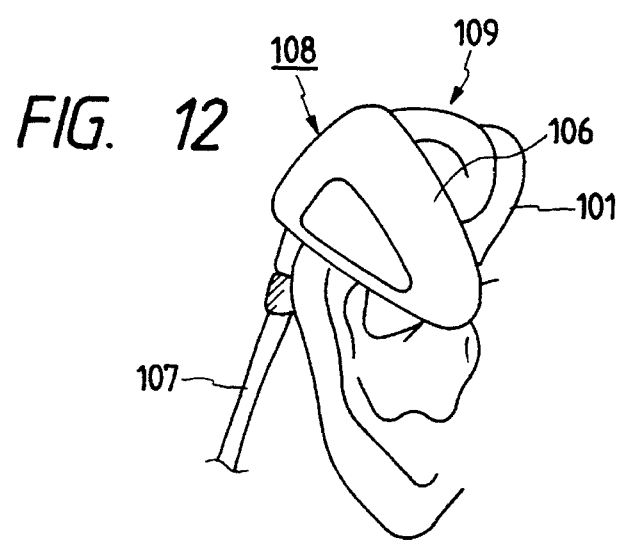
FIG. 12 is a sketch of the front of the ear with the probe attached thereto.
Figure 13:
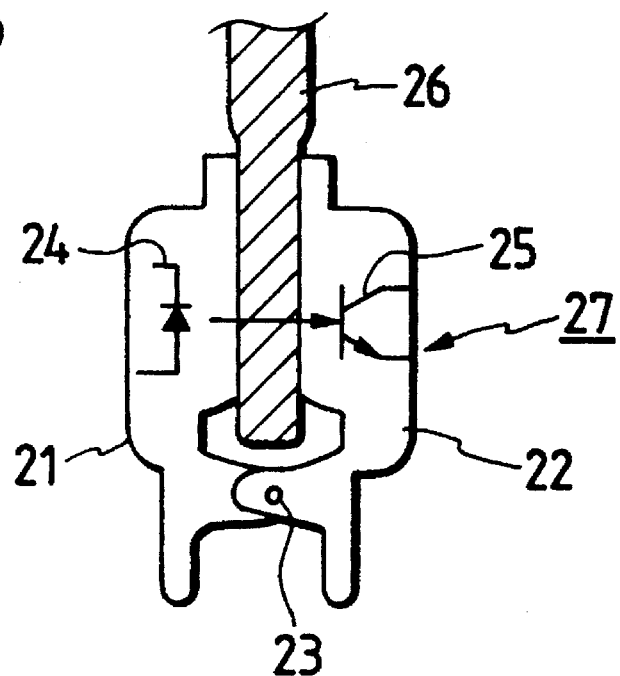
FIG. 13 is a side view showing the construction of a prior art pulse oximeter probe in a clip form that is to be attached to the earlobe of a subject.
Figure 14:
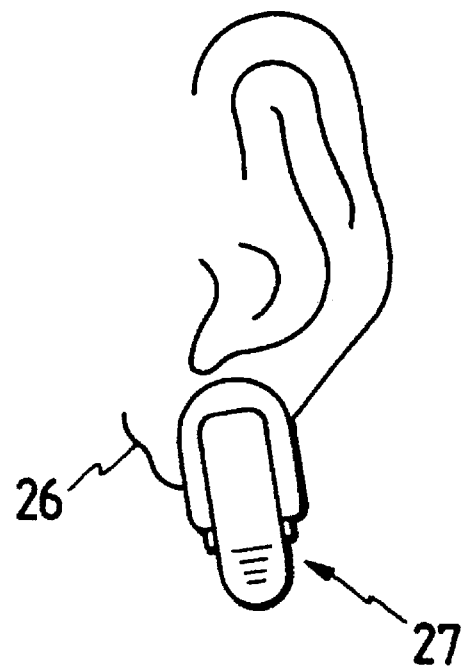
FIG. 14 is a sketch of the probe as it is attached to the earlobe.

The use and operation of the probe under consideration is described below with reference to FIGS. 10 to 20. First, in order to attach the probe 108 to the subject's ear 109, the engaging member 106 is bent upward through an angle of about 90 degrees as indicated by the one-long-and-two-short dashed lines in FIG. 7, and the holding member 101 is placed in engagement with the upper part of the ear 109. Thereafter, the engaging member 106 is bent down to the initial position by pivoting through 90 degrees, and the first pad portion 106a of the engaging member 106 is brought into engagement with the recess 103a formed in the lateral side of the light-receiving element 103, whereby the probe 108 is secured on the ear 109. As a result, the ear 109 has its upper part 109a (see FIGS. 10 and 11) pressed to be held between the second pad portion 106b of the engaging member 106 and the lateral side of the light-emitting element 102. The light-emitting element 102 and the light-receiving element 103 are disposed in a face-to-face relationship holding between themselves the inner recess 109b of the ear 109 which is shown in FIGS. 10 and 11.

In the second embodiment of the present invention described above, the first pad portion 106a of the engaging member 106 engages the recess 103a in the light-receiving element 103, whereby the probe 108 is positioned in such a way that it is securely attached to the ear 109 with its upper part 109a being pressed to be held between the second pad portion 106b of the engaging member 106 and the lateral side of the light-emitting member 102. It should be noted here that the probe 108 can be securely attached to the ear 109 irrespective of the size of the earlobe. It should also be noted that since the light-emitting element 102 and the light-receiving element 103 are disposed on opposite sides of the inner recess 109b of the ear 109 in a face-to-face relationship, the site of measurement is not compressed strongly enough to block the flow of blood through blood vessels; therefore, the pulsation of blood flowing through blood vessels can be detected with a sufficiently high precision to accomplish precise measurement of various blood-related parameters including oxygen saturation, pulse wave, pulse rate and blood pressure.

If desired, the relative positions of the light emitting and light-receiving elements 102 and 103 to be provided on the holding member 101 may be reversed.

As described on the foregoing pages, the pulse oximeter probe according to the second embodiment of the present invention is provided that the upper part of a subject's ear is pressed to be held in position by means of an engaging member and that the position of the holding section is separated from the position of the measuring section which consists of a light-emitting and a light-receiving element as disposed in a face-to-face relationship. This arrangement is effective in preventing excessive movements of the prove without blocking the flow of blood through blood vessels at the site of measurement, thereby insuring the pulsation of blood flow to be detected with high precision.

What is claimed is:

1. A pulse oximeter probe comprising:
   a first holding member having a first compressing portion;
   a second holding member connected to said first holding member and having a second compressing portion, wherein said first and second compressing portions are urged toward each other for holding a part of an ear;
   at least one light emitting element mounted on one of said first and second holding members; and
   a light receiving element mounted on one of said first and second holding members,
   wherein at least one of said light emitting and light receiving elements is mounted on one of said first and second holding members at a position away from the compressing portions so that light which is emitted from said light emitting element travels completely through a portion of the ear which is not compressed by said compressing portions and which is not bordered by ear tissue which is compressed by said compressing portions before reaching said light receiving element, and
   wherein said light emitting and light receiving elements cooperate to form a measuring device.

2. A pulse oximeter probe as claimed in claim 1, wherein the light-emitting element and the light receiving element are mounted on the holding members, respectively to face each other.

3. A pulse oximeter probe as claimed in claim 1 wherein said first compressing portion and said second compressing portion are for holding the basal part of an earlobe, and wherein the first holding member forms at an end thereof a bent portion which is adapted to be inserted into the entrance to the auditory meatus, and wherein one of the light-emitting element and the light-receiving element is mounted on the second compressing portion and the other of the light-emitting and light receiving elements is mounted on the bent portion of the first holding member in such manner that the light-emitting element and the light-receiving element are in a face-to-face relationship.

4. A pulse oximeter probe as claimed in claim 3, wherein each of said holding members has a connecting end away from the respective compressing portions, and wherein one of the two holding members is fitted with a connecting shaft at the connecting end and the connecting shaft is inserted slidably into a slot that is formed at the connecting end of the other holding member.

5. A pulse oximeter probe as claimed in claim 1, wherein each of said holding members has a connecting end away from the respective compressing portions, and wherein one of the two holding members is fitted with a connecting shaft at the connecting end and the connecting shaft is inserted slidably into a slot that is formed at the connecting end of the other holding member.

6. A pulse oximeter probe according to claim 1, wherein:

said first holding member is formed of an elastic material in a generally semicircular form, said light-emitting element and said light-receiving element are provided at opposite ends of said first holding member in a face-to-face relationship; and said second holding member is fitted rotatably at an end of said first holding member, said second holding member including:

a first projection, in the middle portion thereof, for pressing an upper part of an ear and for holding said holding members in position relative to the ear; and a second projection formed at a distal end of said second holding means in such a manner that said second projection is engaged with an end of said first holding member opposite the end at which said first and second holding members are rotatably fitted.

7. A pulse oximeter probe as claimed in claim 6, wherein the light emitting element and the light receiving element positioned away from said first projection.

* * * * *